US008631747B2

(12) United States Patent
Woo et al.

(10) Patent No.: US 8,631,747 B2
(45) Date of Patent: Jan. 21, 2014

(54) HEIGHT ADJUSTMENT DEVICE FOR IMAGING APPARATUS

(75) Inventors: Kyeong Gu Woo, Seoul (KR); Ghi Young Kim, Seoul (KR)

(73) Assignee: Samsung Medison Co., Ltd., Gangwon-Do (KR)

( * ) Notice: Subject to any disclaimer, the term of this patent is extended or adjusted under 35 U.S.C. 154(b) by 952 days.

(21) Appl. No.: 12/760,302

(22) Filed: Apr. 14, 2010

(65) Prior Publication Data

US 2010/0268079 A1 Oct. 21, 2010

(30) Foreign Application Priority Data

Apr. 15, 2009 (KR) .................. 10-2009-0032529
Mar. 26, 2010 (KR) .................. 10-2010-0027135

(51) Int. Cl.
*A47B 9/00* (2006.01)

(52) U.S. Cl.
USPC .............. 108/147; 108/147.19; 248/405

(58) Field of Classification Search
USPC .............. 108/147, 7, 10, 144.11, 147.19; 248/188.5, 161, 422, 405, 406.1
See application file for complete search history.

(56) References Cited

U.S. PATENT DOCUMENTS

| | | | | |
|---|---|---|---|---|
| 1,777,204 A | * | 9/1930 | Korsten et al. | 248/405 |
| 2,176,536 A | * | 10/1939 | McCauley | 248/405 |
| 3,118,705 A | | 1/1964 | Stalnacke | |
| 3,887,155 A | * | 6/1975 | Bertalot | 108/147.19 |
| 3,908,565 A | * | 9/1975 | Burnett | 108/147 |
| 4,651,581 A | * | 3/1987 | Svensson | 74/89.35 |
| 4,793,197 A | | 12/1988 | Petrovsky | |
| 4,860,987 A | * | 8/1989 | Werner | 248/405 |
| 5,282,593 A | * | 2/1994 | Fast | 108/147 |
| 5,322,025 A | * | 6/1994 | Sherman et al. | 108/147 |
| 5,461,974 A | * | 10/1995 | Reneau | 108/147 |
| 5,733,096 A | * | 3/1998 | Van Doren et al. | 414/744.3 |
| 6,286,441 B1 | * | 9/2001 | Burdi et al. | 108/147.19 |
| 6,478,269 B2 | * | 11/2002 | Forsberg | 108/147.19 |
| 6,494,005 B2 | * | 12/2002 | Zimmerman | 108/147 |

(Continued)

FOREIGN PATENT DOCUMENTS

| | | |
|---|---|---|
| DE | 3404300 A1 | 8/1985 |
| JP | S63-083658 A | 4/1988 |
| JP | S63-083658 U | 6/1988 |

OTHER PUBLICATIONS

Extended European Search Report for EP 10159224.4-1265, 6 pages, dated Oct. 6, 2010.

(Continued)

*Primary Examiner* — Jose V Chen
(74) *Attorney, Agent, or Firm* — McDermott Will & Emery LLP (57) ABSTRACT

A height adjustment device for an imaging apparatus includes a driving shaft, first and second moving bodies and a driving device. The driving shaft is configured to rotate in a main body of an imaging apparatus. The driving shaft has first and second spiral grooves defined on a peripheral surface thereof such that the first spiral groove has a first pitch along the driving shaft and a second spiral groove has a second pitch different from the first pitch along the driving shaft. The first moving body has a screw thread engaged with the first spiral groove of the driving shaft. The second moving body has a screw thread engaged with the second spiral groove of the driving shaft The driving device rotates the driving shaft.

9 Claims, 7 Drawing Sheets

(56) References Cited

U.S. PATENT DOCUMENTS

| | | |
|---|---|---|
| 6,663,569 B1 | 12/2003 | Wilkins et al. |
| 7,225,694 B2 * | 6/2007 | Said .............................. 74/89.35 |
| 7,878,476 B2 * | 2/2011 | Carson et al. .................. 248/429 |
| 8,087,737 B2 * | 1/2012 | Shoenfeld ................ 108/147.19 |
| 8,291,840 B2 * | 10/2012 | Baracchia ................ 108/147.19 |
| 2006/0091277 A1 * | 5/2006 | Wang ............................. 248/405 |

OTHER PUBLICATIONS

Korean Notice of Allowance, issued in Korean Patent Application No. 10-2010-0027135, dated Jan. 30, 2012.

* cited by examiner

HEIGHT ADJUSTMENT DEVICE FOR IMAGING APPARATUS

CROSS-REFERENCE TO RELATED APPLICATIONS

This application claims priority from Korean Patent Application No. 10-2009-0032529 filed on Apr. 15, 2010 and Korean Patent Application No. 10-2010-0027135 filed on Mar. 26, 2010, the entire disclosures of each of which are incorporated herein by reference.

TECHNICAL FIELD

The present disclosure generally relates to a height adjustment device for an imaging apparatus, and more particularly to a height adjustment device for simultaneously adjusting a height of and a distance between a control panel and a display device of a medical imaging system such as an ultrasonic diagnostic apparatus.

BACKGROUND

A medical imaging system such as an ultrasonic diagnostic apparatus includes a control panel through which an operator inputs a command and a display device for displaying an image of an ultrasonic diagnosis. Such an ultrasonic diagnostic apparatus is configured such that the control panel and the display device are movable upward and downward to enhance user convenience. For example, the control panel and the display device are configured to move or pivot upward and downward by a link mechanism. As one example of prior art technologies relating to moving the control panel of the display device, U.S. Pat. No. 6,663,569 suggests a device capable of adjusting a position of a control panel equipped to an ultrasonic diagnostic apparatus.

However, a prior art ultrasonic diagnostic apparatus, which can adjust a height of a control panel or a display device, causes inconvenience to an operator in that the operator must individually adjust a height of the control panel and a height of the display device. Further, since the height of the control panel or the display device is individually adjusted by its dedicated mechanism, there is another problem with the prior art ultrasonic diagnostic apparatus in that its structure becomes complicated and its manufacturing cost increases.

As one example of a prior art technology for addressing the foregoing problems, a method of moving one moving part, to which a control panel and a display device are coupled together, is known in the art. However, since both the control panel and the display device are disposed on one moving part and they are moved together by the moving part, the heights or positions of the control panel and the display device cannot be adjusted in harmony with an operator's height or posture, thereby leading to another problem of causing user inconvenience.

SUMMARY

Embodiments of a height adjustment device for an imaging apparatus are disclosed herein. In accordance with one embodiment of the disclosure, a height adjustment device includes a driving shaft, first and second moving bodies and a driving means. The driving shaft is rotatably installed in a main body of an imaging apparatus. The driving shaft includes first and second spiral grooves formed on a peripheral surface thereof. The first spiral groove has a first pitch and the second spiral groove has a second pitch different from the first pitch. The first moving body is screw-engaged to the driving shaft in the first spiral groove, while the second moving body is screw-engaged to the driving shaft in the second spiral groove. The driving means is disposed in the main body and rotates the driving shaft. In one embodiment, the driving shaft includes the first spiral groove formed in one portion thereof and the second spiral groove in another portion in a remaining portion thereof. In another embodiment, the second spiral groove is arranged along with the first spiral groove on the peripheral surface of the driving shaft. A width of the second spiral groove may be different from that of the first spiral groove.

The Summary is provided to introduce a selection of concepts in a simplified form that are further described below in the Detailed Description. This Summary is not intended to identify key features or essential features of the claimed subject matter, nor is it intended to be used to determine the scope of the claimed subject matter.

BRIEF DESCRIPTION OF THE DRAWINGS

Arrangements and embodiments may be described in detail with reference to the following drawings in which like reference numerals refer to like elements and wherein.

DETAILED DESCRIPTION

A detailed description may be provided with reference to the accompanying drawings. One of ordinary skill in the art may realize that the following description is illustrative only and is not in any way limiting. Other illustrative embodiments may readily suggest themselves to such skilled persons having the benefit of this disclosure.

Figure 1:
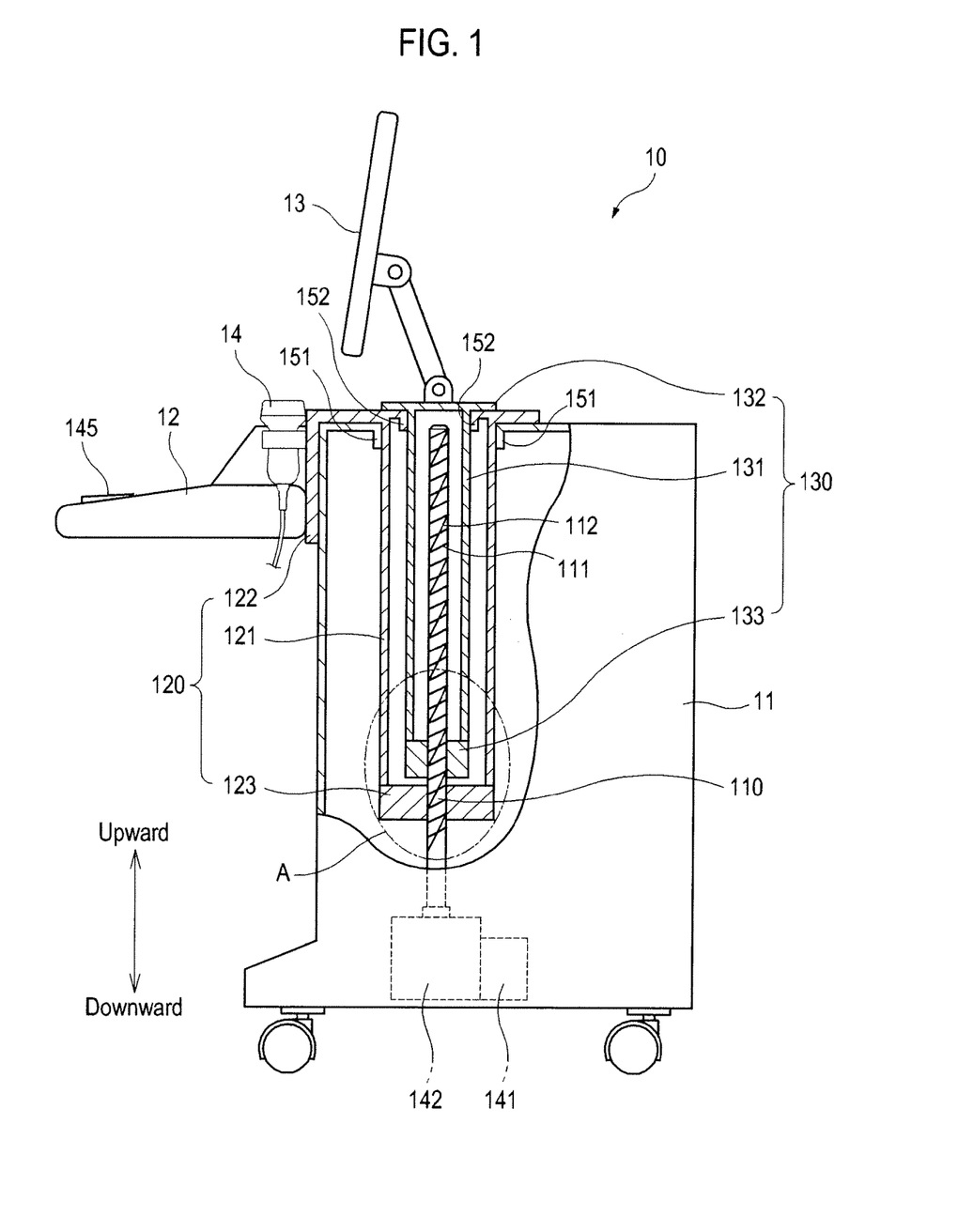
FIG. 1 is a partially cutaway side elevational view of an imaging apparatus including a height adjustment device according to the present disclosure.
Figure 2:
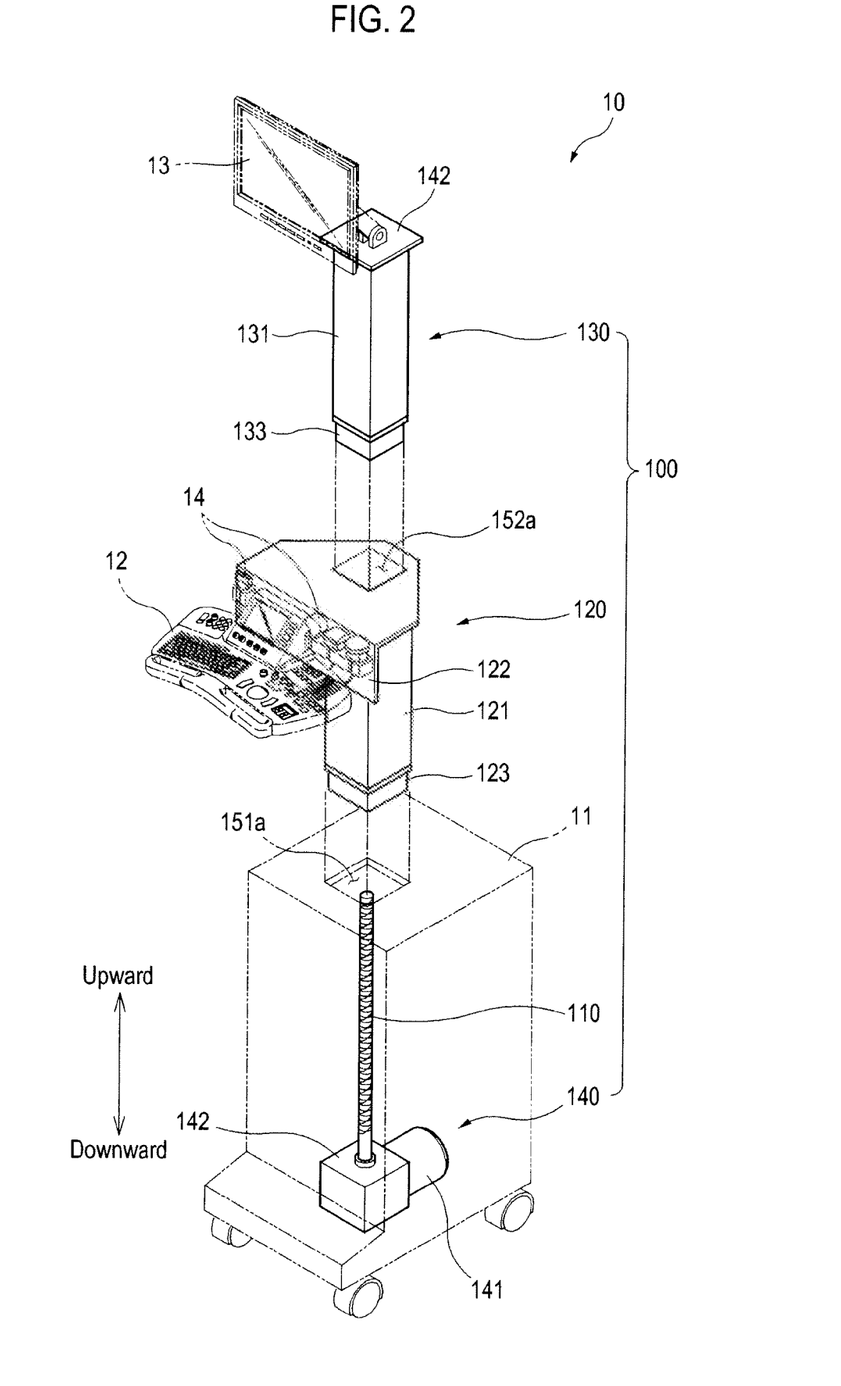
FIG. 2 is an exploded perspective view of the imaging apparatus shown in FIG. 1.

FIG. 1 is a partially cutaway side elevational view of an imaging apparatus including a height adjustment device according to the present disclosure. FIG. 2 is an exploded perspective view of the imaging apparatus shown in FIG. 1. Referring to FIGS. 1 and 2, the height adjustment device 100 according to one embodiment of the present disclosure may be installed in a main body 11 of an ultrasonic diagnostic apparatus 10, which is one example of an imaging apparatus. The main body 11 may accommodate various components or parts for ultrasonic diagnosis therein. The height adjustment device 100 may include the following: a driving shaft 110; first and second moving bodies 120, 130 screw-engaged to the driving shaft 110 and being movable along the driving shaft 110 in a length direction of the driving shaft by screw motion;

and a driving means 140 for rotating the driving shaft 110. Components or parts of an imaging apparatus, which is adjusted in height by the movement of the first and second moving bodies 120, 130, may be coupled to the first and second moving bodies 120, 130. For example, a control panel 12 of the imaging apparatus 10 may be coupled to the first moving body 120, while a display device 13 of the imaging apparatus 10 may be coupled to the second moving body 130.

Figure 3:
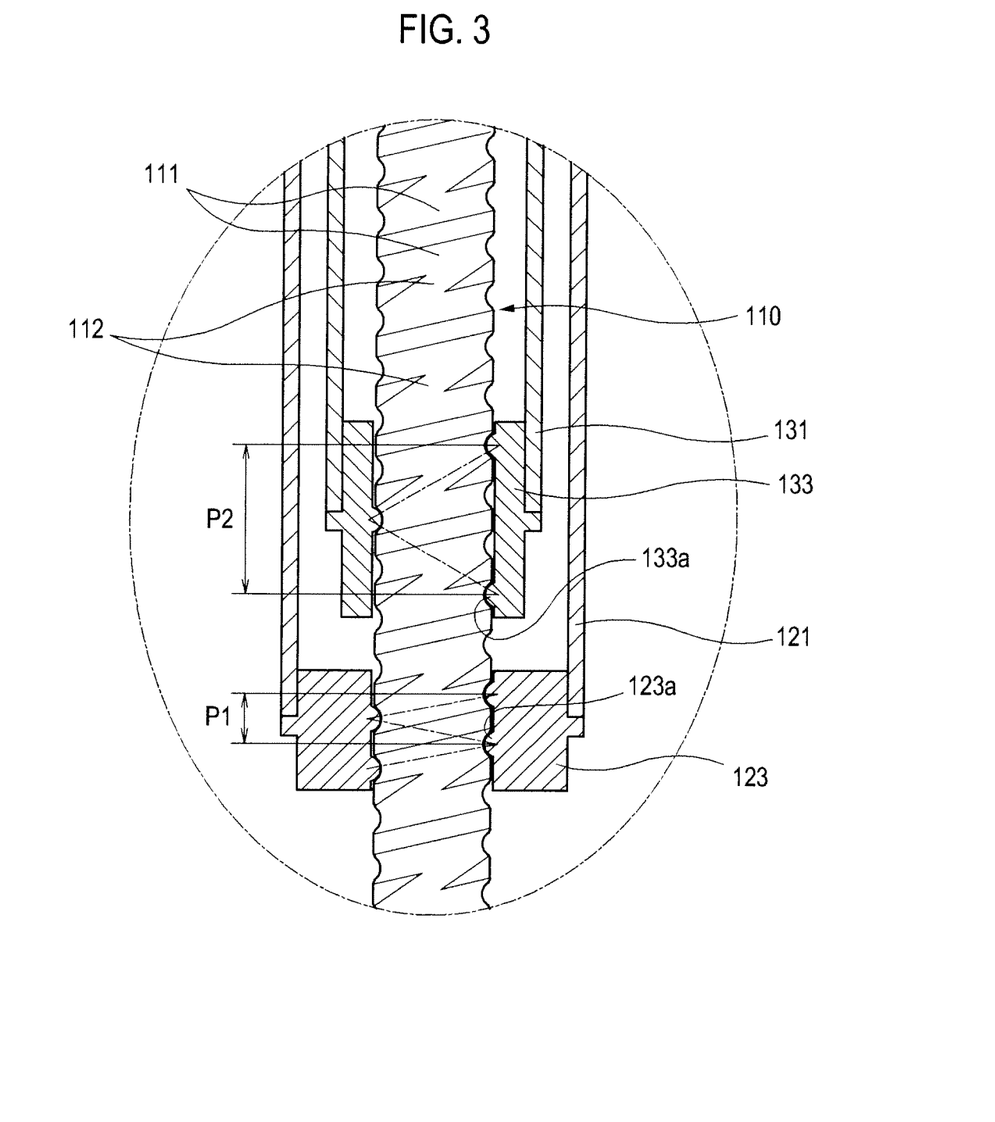
FIG. 3 is an enlarged view of "A" part shown in FIG. 1.

FIG. 3 is an enlarged view of "A" part shown in FIG. 1. Referring to FIGS. 1 to 3, the driving shaft 110 is rotatably supported in the main body 11 and vertically extends therein. The driving shaft 110 may have first and second spiral grooves 111, 112 on a peripheral surface thereof. The first moving body 120 is screw-engaged to the driving shaft 110 in the first spiral groove 111, while the second moving body 130 is screw-engaged to the driving shaft 110 in the second spiral groove 112. As shown in FIG. 3, the first spiral groove 111 may have a first pitch P1, while the second spiral groove 112 may have a second pitch P2. The second pitch P2 may be different from the first pitch P1. In this embodiment, the second pitch P2 is larger than the first pitch P1. A ratio of the first pitch P1 to the second pitch P2 may be determined in consideration of an operator's posture when the operator sits or stands up. Alternatively, the ratio of the first pitch P1 to the second pitch P2 may be determined by considering a distance between the control panel 12 and the display device 13. In the illustrated embodiment, the ratio of the first pitch to the second pitch is about 1:3.

As shown in FIGS. 1 to 3, the first spiral groove 111 is formed throughout an approximate entire length of the driving shaft 110, while the second spiral groove 112 is formed on the first spiral groove 111. Specifically, the second spiral groove 112 is arranged along with the first spiral groove 111 on the peripheral surface of the driving shaft 110. That is, the first spiral groove 111 and the second spiral groove 112 may overlap. Thus, the pitch of the first spiral groove 111 and the pitch of the second spiral groove 112 may coincide with each other at a certain interval. For example, in the illustrated embodiment, the first and second spiral grooves 111, 112 are arranged on the peripheral surface of the driving shaft 110 in such a manner that one pitch of the second spiral groove 112 coincides with three pitches of the first spiral groove 111.

Referring to FIGS. 1 and 2, the height adjustment device 100 may include a first guide part 151 for guiding the first moving body 120 upward and downward relative to the main body 11 and a second guide part 152 for guiding the second moving body 130 upward and downward relative to the main body 11. In the illustrated embodiment, the first guide part 151 is disposed on an upper side of the main body 11, while the second guide part 152 is disposed on an upper side of the first moving body 120. As shown in FIG. 2, the first guide part 151 comprises a first guide wall 151a having a polygonal cross-section, while the second guide part 152 comprises a second guide wall 152a having the same polygonal cross-section as the first guide wall 151a.

The first moving body 120 may be coupled to the main body 11 so as to move upward and downward relative to the main body 11. The first moving body 120 may include: a first tubular member 121 guided by the first guide part 151 to move upward and downward; a supporting portion 122 for supporting the control panel 12 of the imaging apparatus 10; and a first nut member 123 coupled to the first tubular member 121 and being screw-engaged to the driving shaft 110 in the first spiral groove 111.

The first tubular member 121 may have a hollow shape to accommodate a part of the second moving body 130 therein. The first tubular member 121 is guided by the first guide wall 151a to move or carry the first moving body 120 upward and downward relative to the main body 11. The first tubular member 121 has the same polygonal cross-section as the first guide wall 151a so that the first moving body 120 cannot rotate about the driving shaft 110 relative to the main body 11. The supporting portion 122 may be configured to attach probes 14 of the imaging apparatus 10 thereon besides the control panel 12.

As shown in FIG. 3, the first nut member 123 is screw-engaged to the driving shaft 110 in the first spiral groove 111. To this end, a screw thread 123a having the same pitch as the first spiral groove 111 is formed on an inner peripheral surface of the first nut member 123. Thus, as the driving shaft 110 rotates, the first moving body 120 is moved upward and downward by the screw motion caused by the first spiral groove 111 and the first nut member 123.

The second moving body 130 is movable upward and downward relative to the main body 11 as inserted into the first moving body 120. The second moving body 130 may include: a second tubular member 131 guided by the second guide part 152 to move upward and downward; a supporting portion 132 for supporting the display device 13 of the imaging apparatus 10; and a second nut member 133 coupled to the second tubular member 131 and screw-engaged to the driving shaft 110 in the second spiral groove 112.

While the second tubular member 131 is guided by the guide wall 152a of the first tubular member 121 to move inward and outward of the first tubular member 121, the second tubular member 131 moves or carries the second moving body 130 upward and downward relative to the main body 11 or the first moving body 120. The second tubular member 131 has the same polygonal cross-section as the second guide wall 152a so that the second moving body 130 cannot rotate about the driving shaft 110 relative to the main body 11.

In the embodiment shown in FIG. 1, the driving shaft 110 extends along central axes of the first and second tubular members 121, 131. In other embodiment, the driving shaft 110 may be offset or be eccentric from the central axes of the first and second tubular members 121, 131.

As shown in FIG. 3, the second nut member 133 is screw-engaged to the driving shaft 110 in the second spiral groove 112. To this end, a screw thread 133a having the same pitch as the second spiral groove 112 is formed on an inner peripheral surface of the second nut member 133. Thus, as the driving shaft 110 rotates, the second moving body 120 is moved upward and downward by the screw motion caused by the second spiral groove 112 and the second nut member 133.

Figure 4:
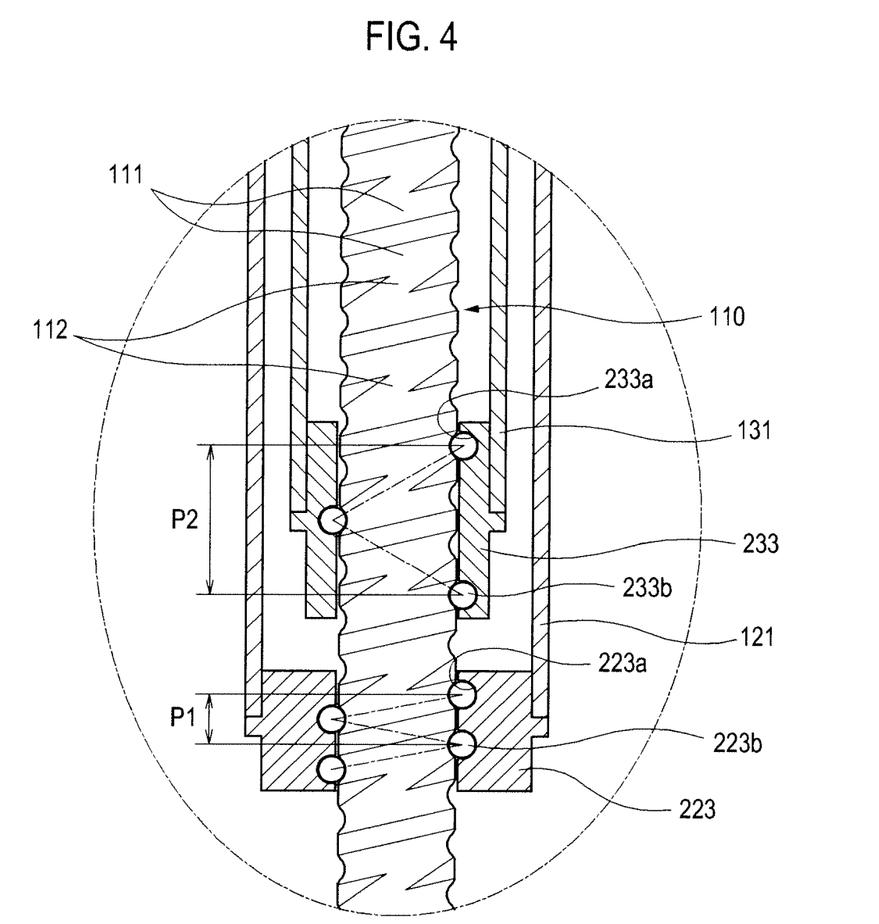
FIG. 4 shows nut members according to another embodiment.

FIG. 4 shows nut members according to another embodiment. As shown in FIG. 4, to ensure a smooth screw motion between the driving shaft 110 and the nut members, first and second nut members 223, 233 may include: spiral grooves 223a, 233a having the same pitches as respective pitches of the first and second spiral grooves 111, 112; and balls 223b, 233b received in the spiral grooves 223a, 233a to roll on the first and second spiral grooves 111, 112 of the driving shaft 110.

Further, in the embodiment shown in FIGS. 1 to 4, the first nut member 123, 223, which is screw-engaged to the first spiral groove 111 and has a smaller first pitch, is provided at the first moving body 120. Also, the second nut member 133, 233, which is screw-engaged to the second spiral groove 112 and has a larger second pitch than the first pitch, is provided at the second moving body 130. In other embodiment, a first nut member may be provided at the second moving body, while the second nut member may be provided at the first moving body. In such a case, the second moving body can move more slowly than the first moving body.

Further, the first spiral groove 111 may have a different width or depth from that of the second spiral groove 112. For example, when a width and/or depth of a spiral groove having a larger pitch is wider and/or deeper than that of a spiral groove having a smaller pitch, a nut member, which is screw-engaged to the spiral groove having the larger pitch, can be subjected to less interference with the spiral groove having the smaller pitch.

Figure 5:
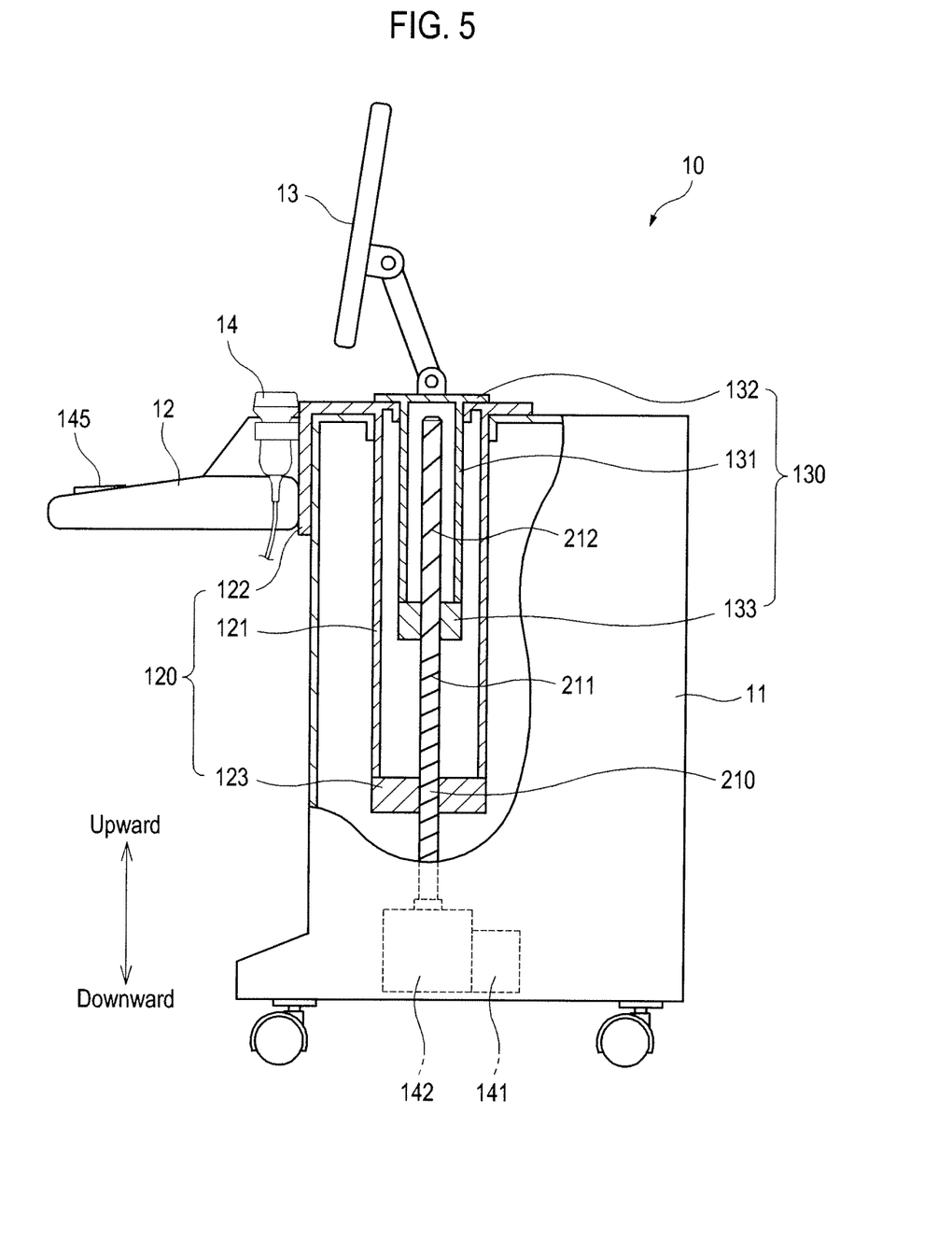
FIG. 5 shows an imaging apparatus including a driving shaft according to another embodiment.

FIG. 5 shows a driving shaft according to another embodiment. A driving shaft 210 may include a first spiral groove formed in one portion thereof and a second spiral groove formed in another portion in a remaining portion thereof. For example, as shown in FIG. 5, a first spiral groove 211 is formed at a lower portion of the driving shaft 210, while a second spiral groove 212 is formed at an upper portion of the driving shaft 210. In this case, when compared to the embodiment shown in FIG. 3 wherein the second spiral groove 112 is arranged along with the first spiral groove 111 on the peripheral surface of the driving shaft 110, the second spiral groove 212 may have a more various shape, pitch and width.

Figure 6:
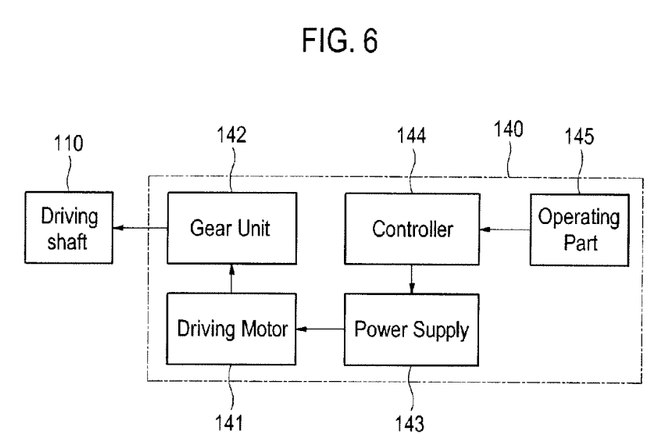
FIG. 6 is a block diagram showing a constitution of a driving means of the height adjustment device shown in FIG. 1.

FIG. 6 is a block diagram showing a constitution of a driving means of the height adjustment device shown in FIG. 1. Referring to FIGS. 1 and 6, the driving means 140 may include: a driving motor 141 installed in the main body 11; a gear unit 142 for connection between the driving shaft 110 and the driving motor 141; a power supply 143 for supplying an electric power to the driving motor 141; a controller 144 for controlling the power supply 143; and an operating part 145 for inputting a command to the controller 144. With the above-described constitution, the driving means 140 rotates the driving shaft 110 in an electrically operable manner.

For example, the driving motor 141 may comprise a step motor to achieve a precise rotation of the driving shaft 110. The gear unit 142 may serve to transmit a rotational driving force of the driving motor 141 to the driving shaft 110. The gear unit 142 may comprise a gear box or a gear train including a plurality of gears. Further, the gear of the gear unit 142 may include a spur gear, a worm gear, a bevel gear, etc. The rotational driving force of the driving motor 141 may be increased by the gear unit 142 and then transmitted to the driving shaft 110. In another embodiment, the driving means 140 may be configured in such a manner that a rotating shaft of the driving motor 141 is directly coupled to the driving shaft 110.

The controller 144 may control the power supply 143 based on a command inputted from the operating part 145. Under the control of the controller 144, the power supply 143 may supply the electric power to the driving motor 141 and determine a driving direction of the driving motor 141.

The operating part 145 may have a push button. The operating part 145 may be disposed on the control panel 12 of the imaging apparatus 10 (see FIG. 1). The operating part 145 may be disposed at any location of the main body 11. The controller 144 and the operating part 145 may be connected to each other in a wired or wireless manner. When an operator manipulates the operating part 145, the controller 144 controls the power supply 143 to supply the electric power to the driving motor 141. Then, the driving motor 141 rotates in one direction and the rotational driving force of the driving motor 141 is transmitted to the driving shaft 110 through the gear unit 142, thereby rotating the driving shaft 110. Thus, the first and second moving bodies 120, 130, which are screw-engaged to the first and second spiral grooves 111, 112 of the driving shaft 110 via the first and second nut members 123, 133, are allowed to move upward and downward by the rotation of the driving shaft 110. In such a case, the first moving body 120 and the second moving body 130 are moved at different velocities and by different distances.

Figure 7:
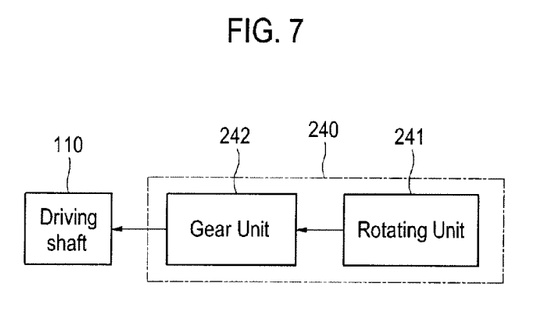
FIG. 7 is a block diagram showing a constitution of a driving means of the height adjustment device according to another embodiment.

FIG. 7 is a block diagram showing a constitution of a driving means of the height adjustment device according to another embodiment. Referring to FIG. 7, a driving means 240 may manually rotate the driving shaft 110. The driving means 240 may include: a rotating unit 241 rotatably installed on the main body 11; and a gear unit 242 for connection between the rotating shaft 110 and the rotating unit 241. The rotating unit 241 may include: a rotating wheel exposed outward of the main body 11; and a rotating shaft coupled to the rotating wheel to rotate together with the rotating wheel.

The gear unit 242 may connect the rotating shaft of the rotating wheel to the driving shaft 110 to transmit a rotational driving force caused by the rotating wheel to the driving shaft 110. The gear unit 242 may be configured similarly to the gear unit 142 of the driving means 140. When an operator rotates the rotating wheel of the rotating unit 241 in one direction or opposite direction, the rotational driving force of the rotating wheel is transmitted to the driving shaft 110 through the gear unit 242 and the rotating shaft 110 rotates to move the first and second moving bodies 120, 130.

Figure 8:
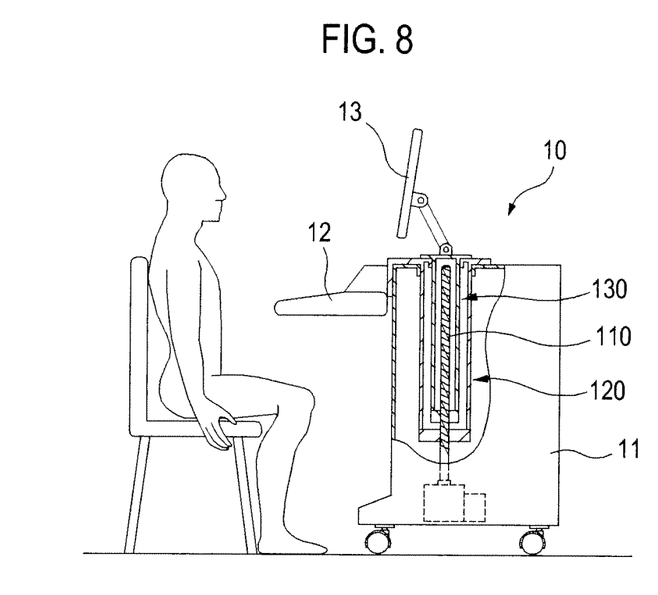
FIG. 8 illustrates positions of a control panel and a display device when an operator sits down.
Figure 9:
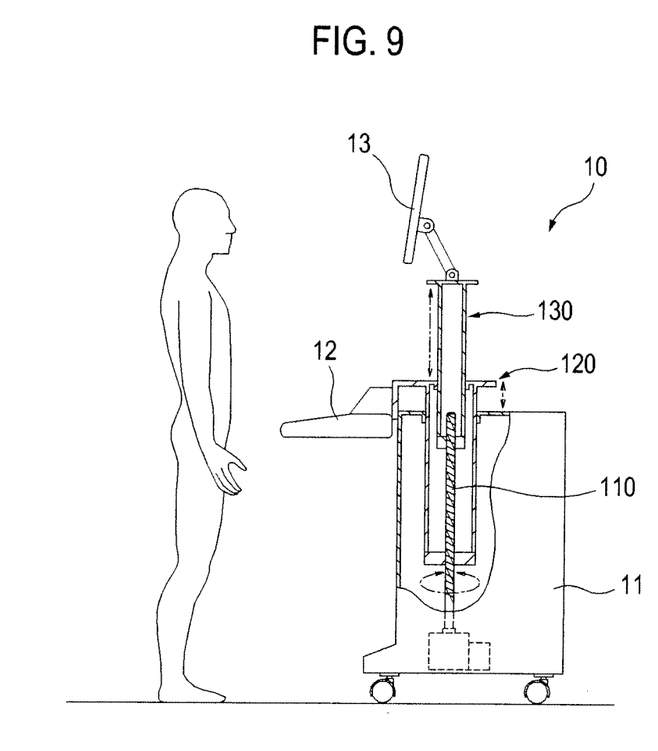
FIG. 9 illustrates positions of a control panel and a display device when an operator stands up.

FIG. 8 illustrates positions of a control panel and a display device when an operator sits down. FIG. 9 illustrates positions of a control panel and a display device when an operator stands up. Referring to FIGS. 8 and 9, the height adjustment device 100 according to the present disclosure may move the first and second moving bodies 120, 130 at different velocities and by different distances by means of the driving shaft 110 having the first and second spiral grooves 111, 112. Thus, it is possible to simultaneously adjust the heights of the control panel 12 and the display device 13 as well as the distance between the control panel 12 and the display device 13. Accordingly, when the operator sits down or stands up, the heights and positions of the control panel 12 and the display device 13 can be adjusted in harmony with the operator' posture.

According to the height adjustment device of the present disclosure, the height of the control panel 12 and the display device 13 of the imaging apparatus 10 and the distance therebetween can be adjusted simultaneously and easily in harmony with an operator's height or posture by means of the driving shaft 110, 210 which is driven in the electrically operable or manual mode.

Although embodiments have been described with reference to a number of illustrative embodiments thereof, it should be understood that various other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A height adjustment device for an imaging apparatus, comprising:
   a driving shaft configured to rotate in a main body of the imaging apparatus and having first and second spiral grooves defined on a peripheral surface thereof such that the first spiral groove has a first pitch along the driving shaft and the second spiral groove has a second pitch different from the first pitch along the driving shaft;

a first moving body having a screw thread engaged with the first spiral groove of the driving shaft to move along the driving shaft by rotation of the driving shaft;

a second moving body having a screw thread engaged with the second spiral groove of the driving shaft to move along the driving shaft by rotation of the driving shaft; and a driving device disposed in the main body and configured to rotate the driving shaft.

2. The height adjustment device of claim 1, wherein the driving shaft includes the first spiral groove in one portion thereof and the second spiral groove in another portion in a remaining portion thereof.

3. The height adjustment device of claim 1, wherein the second spiral groove is arranged along with the first spiral groove on the peripheral surface of the driving shaft in an overlapping manner.

4. The height adjustment device of claim 3, wherein a width of the second spiral groove is different from a width of the first spiral groove.

5. The height adjustment device of claim 1, further comprising:

a first guide part configured to guide the first moving body relative to the main body such that the first moving body is guided to move upward and downward along the driving shaft; and a second guide part configured to guide the second moving body relative to the main body such that the second moving body is guided to move upward and downward along the driving shaft, wherein:

the first moving body includes:
a first tubular member movable upward and downward as guided by the first guide part; and
a first nut member coupled to the first tubular member and having the screw thread engaged with the first spiral groove of the driving shaft, and the second moving body includes:
a second tubular member movable upward and downward as guided by the second guide part; and
a second nut member coupled to the second tubular member and having the screw thread engaged with the second spiral groove of the driving shaft.

6. The height adjustment device of claim 5, wherein the first guide part comprises a first guide wall disposed in the main body and having a polygonal cross-section, wherein the first tubular member has the same polygonal cross-section as the first guide wall and moves through the first guide wall, wherein the second guide part comprises a second guide wall disposed at an upper end of the first tubular member and having a polygonal cross-section, and wherein the second tubular member has the same polygonal cross-section as the second guide wall and moves through the second guide wall.

7. The height adjustment device of claim 1, wherein the driving device includes a driving motor, and a gear connecting between the driving motor and the driving shaft such that the driving motor rotates the driving shaft through the gear.

8. The height adjustment device of claim 1, wherein the driving device includes a rotating unit rotatably disposed on the main body, and a gear connecting between the rotating unit and the driving shaft such that the rotating unit rotates the driving shaft through the gear.

9. The height adjustment device of claim 1, wherein:

the imaging apparatus comprises an ultrasonic diagnostic apparatus having a control panel and a display device, and the control panel is coupled to the first moving body and the display device is coupled to the second moving body.

* * * * *